United States Patent [19]
Underwood et al.

[11] Patent Number: 6,150,559
[45] Date of Patent: Nov. 21, 2000

[54] PROCESS FOR THE PRODUCTION OF BIS (N,N-DIALKYLAMINOALKYL) ETHER

[75] Inventors: Richard Paul Underwood, Allentown; Hong-Xin Li, Landsdale, both of Pa.

[73] Assignee: Air Products and Chemicals, Inc., Allentown, Pa.

[21] Appl. No.: 09/431,912

[22] Filed: Nov. 2, 1999

[51] Int. Cl.$^7$ .................................................. C07C 85/24
[52] U.S. Cl. ............................................................ 564/508
[58] Field of Search ............................................. 564/508

[56] References Cited

U.S. PATENT DOCUMENTS

| | | | |
|---|---|---|---|
| 4,177,212 | 12/1979 | Poppelsdorf | 260/584 R |
| 4,247,482 | 1/1981 | Poppelsdorf | 564/508 |
| 4,474,988 | 10/1984 | Kaiser | 564/508 |
| 5,214,142 | 5/1993 | King | 544/111 |

OTHER PUBLICATIONS

Ziolek, et al., *Catalysis Letters*, vol. 37, pp. 223–227, 1996.
Barrault, et al., *Catalysis of Organic Reactions*, Edited by Frank Herkes, pp. 13–23, Dekker, 1998 Month Unavailable.

*Primary Examiner*—Samuel Barts
*Attorney, Agent, or Firm*—Mary E. Bongiorno

[57] ABSTRACT

An improved process for the production of bis (N,N-dialkylaminoalkyl)ether having the formula $(R_2NR')_2O$, wherein R is methyl or ethyl and R' is ethyl or propyl, by reacting vaporized N,N-dialkylaminoalkanol of the formula $R_2NR'OH$, wherein R and R' are as defined above, in the presence of a heterogeneous solid basic catalyst. The bis (N,N-dialkylaminoalkyl)ether compounds, especially bis (N,N-dimethylamino)ethyl ether, are useful in the production of polyurethane foams.

12 Claims, No Drawings

PROCESS FOR THE PRODUCTION OF BIS (N,N-DIALKYLAMINOALKYL) ETHER

BACKGROUND OF THE INVENTION

Bis (N,N-dialkylaminoalkyl) ethers of the formula $(R_2NR')_2O$, in which R is a methyl or ethyl group and R' is ethyl or propyl, are useful in the production of polyurethanes, especially polyurethane foams. One member of this family of compounds—bis (N,N-dimethylaminoethyl) ether (BDMAEE)—is an industry-standard polyurethane catalyst. It is primarily used to catalyze the blowing reaction, i.e., the reaction of isocyanate and water to produce $CO_2$, in the production of flexible polyurethane foam.

The are several known processes for producing bis (N,N-dialkylaminoalkyl) ethers, including BDMAEE. For example:

U.S. Pat. No. 4,177,212 (Poppelsdorf, 1979) discloses a two-step, one pot reaction for producing bis (N,N-dialkylamino)alkyl ethers in which sodio N,N-dialkylaminoalkoxide is reacted with a sulfur oxychloro-containing compound selected from sulfuryl chloride, thionyl choride or chlorosulfonic acid, in the presence of an organic diluent/dispersant and an N,N-dialkylaminoalkanol. The intermediate reaction product is heated to an elevated temperature to produce the bis (N,N-dialkylamino)alkyl ether. This process has disadvantages including disposal problems associated with by-product salt and special handling required for the chloro-containing compound.

U.S. Pat. No. 4,247,482 (Poppelsdorf, 1981) discloses a process similar to the process described in U.S. Pat. No. 4,177,212 except that $SO_3$ vapor is used in place of the sulfur oxychloro-containing compound. Besides the problems associated with isolation and disposal of the by-product sodium sulfate, an additional disadvantage of this process is the problems associated with handling the toxic and corrosive $SO_3$.

U.S. Pat. No. 4,474,988 (Kaiser, 1984) discloses production of bis (N,N-dialkylamino)alkyl ethers by reacting (N,N-dialkylamino)alkanol over a heterogeneous solid acid catalyst. This process has the drawback of producing several by-products due to low selectivity.

U.S. Pat. No. 5,214,142 (King, 1993) discloses a process for preparing bis[2-(N,N-dialkylamino)alkyl]ethers by contacting a carboxylated aminoether with a metal oxide catalyst. The aminoethers are prepared by contacting an active hydrogen-containing compound, such as an alcohol, with a carbon dioxide synthon in the presence of a metal oxide catalyst.

The use of basic zeolites in the dehydrative etherification of alcohols is known in the art. For example, Ziolek, et al. (*Catalysis Letters,* Vol. 37, pages 223–227, 1996) disclose the preparation of dimethyl ether from the reaction of methanol in the presence of NaY zeolite. Barrault, et al. (In *Catalysis of Organic Reactions,* edited by Frank Herkes, pages 13–23, Dekker, 1998) report the etherification of glycerol to di- and triglycerols in the presence of basic zeolite catalysts, including sodium, potassium, and cesium exchanged Y zeolite. However, there are no known references to etherification of alcohols containing amine functionality using a basic zeolite catalyst.

BRIEF SUMMARY OF THE INVENTION

This invention is directed to an improved process for the production of bis (N,N-dialkylaminoalkyl)ether having the formula $(R_2NR')_2O$, wherein R is methyl or ethyl and R' is ethyl or propyl, by reacting N,N-dialkylaminoalkanol of the formula $R_2NR'OH$, wherein R and R' are as defined above, in the presence of a heterogeneous solid basic catalyst. Specifically it is directed to production of bis (N,N-dimethylaminoethyl) ether (BDMAEE) by reacting vaporized N,N-dimethylaminoethanol (DMAE) in the presence of a heterogeneous solid basic catalyst. More particularly, this invention pertains to a process which utilizes a catalyst consisting of a zeolite in an alkali metal cation form to affect the dehydrative etherification of DMAE to BDMAEE. In the process of this invention, a vaporized form of the N,N-dialkylaminoalkanol is contacted with a heterogeneous solid basic catalyst at elevated temperatures.

Use of the process of this invention results in high selectivity in production of bis (N,N-dialkylaminoalkyl) ether; and high selectivity results in better use of reactants and simpler downstream separation of product.

DETAILED DESCRIPTION OF THE INVENTION

This invention is an improved process for the production of bis (N,N-dialkylaminoalkyl)ether having the formula $(R_2NR')_2O$, wherein R is methyl or ethyl and R' is ethyl or propyl. The process comprises the direct reaction of an N,N-dialkylaminoalkanol of the formula $R_2NR'OH$, wherein R and R' are as defined above, in the presence of a heterogeneous solid basic catalyst. Preferably, the N,N-dialkylaminoalkanol is N,N-dimethylaminoethanol and the product is bis (N,N-dimethylaminoethyl)ether.

N,N-dialkylaminoalkanol compounds are well known in the art and are commercially available. They can be prepared by a variety of well known methods.

The process of the present invention is carried out by reacting vaporized N,N-dialkylaminoalkanol in the presence of a solid base catalyst. The type of reactor used to affect the conversion is not critical, but a preferred embodiment employs a fixed bed reactor, due to its relative simplicity. The N,N-dialkylaminoalkanol is vaporized by heating it to a temperature above its boiling point at reaction pressure and passing the vaporized compound through the reaction zone. Prior to vaporization of the N,N-dialkylaminoalkanol or introduction of the N,N-dialkylaminoalkanol to the reaction zone, the N,N-dialkylaminoalkanol can optionally be mixed with a solvent, such as water or a gas, such as nitrogen, helium, argon, and hydrogen. The catalyst and reactants are heated to an elevated temperature for effective conversion of the N,N-dialkylaminoalkanol. Temperatures of 250° C. to 500° C. are generally sufficient, the preferred temperature range being about 350° C. to 425° C. The reaction pressure employed is not believed to be critical and the process can likely be operated over a broad pressure range, from vacuum up to many times atmospheric pressure. The fraction of the feed N,N-dialkylaminoalkanol which reacts will depend on the feed rate, typically decreasing with increasing feed rate. However, practical conversion can be obtained for feed rates ranging from 0.1 to 10 volumes of liquid N,N-dialkylaminoalkanol per catalyst volume per hour.

The catalysts used in the present invention are important in achieving high selectivity to the bis (N,N-dialkylaminoalkyl)ether. These catalysts are basic solids. Preferably, the catalyst employed is a zeolite in an alkali metal cation form. Examples of such zeolites include aluminosilicates of the faujasite type (X or Y) in the lithium, sodium, potassium, rubidium, or cesium ion form, or in a mixed alkali metal cation form. A preferred zeolite is the X type zeolite. These zeolites are typically manufactured and are commercially available in the sodium form. Transformation to another alkali metal form can be carried out using any of the well known methods established in the industry, such as ion exchange. Transformation to another alkali metal form may not result in complete conversion; thus, the zeolite may contain more than one alkali metal cation.

The invention will be further clarified by a consideration of the following examples, which are intended to be purely exemplary of the invention.

EXAMPLE 1

Preparation of NaX Zeolite

Linde 13x powder (as received) was pressed into aggregates, then the aggregates were crushed and sized by sieving. The particle size fraction between 18 mesh and 35 mesh was used in Example 6.

EXAMPLE 2

Preparation of Potassium-treated X Zeolite Catalyst

Linde 13x zeolite powder (10 g) was slurried in 300 ml of a 1 molar solution of potassium acetate in a PTFE bottle. The bottle was placed in an oven maintained at 90° C. for 16 hr. The slurry was then allowed to cool, vacuum filtered, and washed with de-ionized water. The filter cake was then added back to the bottle and mixed with a fresh 300 ml of 1 molar potassium acetate solution and placed in the 90° C. oven for an additional 16 hr. The slurry was allowed to cool, vacuum filtered, and washed with water. The filter cake was dried in an oven at 110° C. for 2 hr, then calcined in air at 500° C. for 3.5 hr. The calcined powder contained 19.6 wt % potassium by elemental analysis. The resulting calcined powder was pressed into aggregates, and the aggregates were crushed and sized by sieving. The particle size fraction between 18 mesh and 35 mesh was used in Example 6.

EXAMPLE 3

Preparation of Cesium-treated X Zeolite Catalyst

Linde 13x zeolite powder (8.7 g) was slurried in 260 ml of a 1 molar solution of cesium acetate in a PTFE bottle. The bottle was placed in an oven maintained at 90° C. for 16 hr. The slurry was then allowed to cool, vacuum filtered, and washed with de-ionized water. The filter cake was then added back to the bottle and mixed with a fresh 260 ml of 1 molar cesium acetate solution and placed in the 90° C. oven for an additional 16 hr. The slurry was allowed to cool, vacuum filtered, and washed with water. The filter cake was dried in an oven at 90° C. for 16 hr. The dried powder was then pressed into aggregates, and the aggregates were crushed and sized by sieving. The particle size fraction between 18 mesh and 35 mesh was calcined in air at 500° C. for 3.5 hr and used in Example 6. This material contained 32.5 wt % cesium by elemental analysis.

EXAMPLE 4

Preparation of NaY Zeolite

NaY zeolite powder from Aldrich was heated to 500° C. and held at that temperature for 3.5 hr. The powder was allowed to cool, pressed into aggregates, then the aggregates were crushed and sized by sieving. The particle size fraction between 18 mesh and 35 mesh was calcined in air at 500° C. for 3.5 hr and used in Example 6.

COMPARATIVE EXAMPLE 5

Preparation of Gamma-Alumina

LaRoche A-201 activated $\gamma$-$Al_2O_3$ powder (as received) was pressed into aggregates, and the aggregates were crushed and sized by sieving. The particle size fraction between 18 mesh and 35 mesh was used in Comparative Example 7.

EXAMPLE 6

Conversion of DMAE was carried out using a 0.64 cm I.D. stainless-steel, continuous flow tubular reactor. Approximately, 1–2 $cm^3$ of catalyst particles from Examples 1–4 were loaded into the reactor between 2 layers of 18–35 mesh quartz chips. The bottom layer of quartz served as a catalyst bed support, while the top layer provided a surface on which the DMAE feed was vaporized. The reactor was inserted into a tubular, electric, temperature-controlled furnace. The DMAE feed was supplied to the top of the reactor by means of a HPLC pump and nitrogen carrier was also supplied upstream by means of a mass flow controller. The liquid reactor product was condensed and sampled downstream from the reactor and analyzed off-line by capillary FID gas chromatography.

Tables 1–4 show results for the reaction of DMAE, at various temperatures, using the catalysts from Examples 1–4.

TABLE 1

NaX (13X) Zeolite
Pressure = 1 atm, DMEA Feed Rate = 2.7 g/hr, $N_2$ flow = 9 sccm
catalyst weight = 1.72 g

| | Temperature (° C.) | | |
|---|---|---|---|
| | 350 | 375 | 400 |
| DMEA Conversion (%) | 39 | 61 | 56 |
| Molar Selectivity (%) | | | |
| BDMAEE | 25 | 34 | 50 |
| DMP | 6 | 7 | 5 |
| NMM | 12 | 11 | 5 |
| TMEDA | 8 | 9 | 9 |

DMAE = N,N-dimethylamino-ethanol 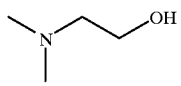

BDMAEE = bis(N,N-dimethyl-aminoethyl)ether 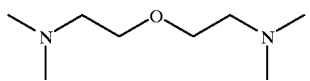

DMP = N,N'-dimethylpiperazine 

NMM = N-methylmorpholine 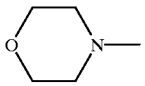

TMEDA = N,N,N',N'-tetra-methyl-1,3-ethanediamine 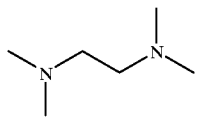

TABLE 1-continued

NaX (13X) Zeolite
Pressure = 1 atm, DMEA Feed Rate = 2.7 g/hr, N₂ flow = 9 sccm
catalyst weight = 1.72 g $$\text{DMAEConversion} = 100\% \times \frac{\text{molesDMAEreacted}}{\text{molesDMAEfed}}$$

$$\text{BDMAEESelectivity} = 100\% \times \frac{2 \times \text{molesBDMAEEproduced}}{\text{molesDMAEconverted}}$$

$$\text{DMPSelectivity} = 100\% \times \frac{2 \times \text{molesDMPproduced}}{\text{molesDMAEconverted}}$$

$$\text{NMM Selectivity} = 100\% \times \frac{2 \times \text{moles}NMM\text{produced}}{\text{molesDMAEconverted}}$$

$$\text{TMEDASelectivity} = 100\% \times \frac{\text{molesTMEDA}produced}{\text{molesDMAEconverted}}$$

TABLE 2

K-treated 13X Zeolite
Pressure = 1 atm, DMEA Feed Rate = 2.7 g/hr, N₂ flow = 9 sccm
catalyst weight = 1.72 g

|  | Temperature (° C.) | | | |
| --- | --- | --- | --- | --- |
|  | 350 | 375 | 400 | 425 |
| DMEA Conversion (%) Molar Selectivity (%) | 19 | 33 | 56 | 52 |
| BDMAEE | 39 | 59 | 55 | 49 |
| DMP | 6 | 5 | 4 | 3 |
| NMM | 6 | 4 | 3 | 2 |
| TMEDA | 8 | 7 | 7 | 7 |

TABLE 3

Cs-treated 13X Zeolite
Pressure = 1 atm, DMEA Feed Rate = 2.7 g/hr, N₂ flow = 9 sccm
catalyst weight = 1.72 g

|  | Temperature (° C.) | | | |
| --- | --- | --- | --- | --- |
|  | 350 | 375 | 400 | 425 |
| DMEA Conversion (%) Molar Selectivity (%) | 37 | 60 | 66 | 56 |
| BDMAEE | 41 | 46 | 46 | 36 |
| DMP | 9 | 7 | 5 | 3 |
| NMM | 6 | 4 | 3 | 2 |
| TMEDA | 9 | 9 | 9 | 7 |

TABLE 4

NaY Zeolite
Pressure = 1 atm, DMEA Feed Rate = 2.7 g/hr, N₂ flow = 9 sccm
catalyst weight = 1.71 g

|  | Temperature (° C.) | | | |
| --- | --- | --- | --- | --- |
|  | 350 | 375 | 400 | 425 |
| DMEA Conversion (%) Molar Selectivity (%) | 20 | 23 | 40 | 43 |
| BDMAEE | 3 | 11 | 18 | 26 |
| DMP | 5 | 6 | 6 | 5 |

TABLE 4-continued

NaY Zeolite
Pressure = 1 atm, DMEA Feed Rate = 2.7 g/hr, N₂ flow = 9 sccm
catalyst weight = 1.71 g

|  | Temperature (° C.) | | | |
| --- | --- | --- | --- | --- |
|  | 350 | 375 | 400 | 425 |
| NMM | 4 | 11 | 12 | 5 |
| TMEDA | 3 | 7 | 8 | 7 |

COMPARATIVE EXAMPLE 7

Table 5 shows the results for conversion of DMAE using an acid catalyst, activated gamma-Al₂O₃. Experimental methodology is the same as described in Example 6.

TABLE 5 gamma-Al₂O₃
Pressure = 1 atm, DMEA Feed Rate = 3.6 g/hr, N₂ flow = 9 sccm
catalyst weight = 1 g

|  | Temperature (° C.) | | | |
| --- | --- | --- | --- | --- |
|  | 250 | 275 | 300 | 325 |
| DMEA Conversion (%) Molar Selectivity (%) | 11 | 18 | 36 | 62 |
| BDMAEE | 6 | 15 | 16 | 14 |
| DMP | 1 | 6 | 10 | 9 |
| NMM | 1 | 4 | 6 | 4 |
| TMEDA | 1 | 3 | 6 | 7 |

The data in Tables 1–5 show that, unexpectedly, the basic X and Y zeolites of examples 1–4 (Tables 1–4) show very good conversion of DMAE and very good selectivity to BDMAEE, compared to the acid catalyst (gamma-alumina) of comparative example 5 (Table 5).

What is claimed is:

1. A process for producing bis (N,N-dialkylamino)alkyl ether having the formula, (R₂NR')₂O
   wherein R is methyl or ethyl and R' is ethyl or propyl, comprising reacting vaporized N,N-dialkylaminoalkanol of the formula, R₂NR'OH, 

wherein R and R' are as defined above, at elevated temperature in the presence of a heterogeneous solid basic catalyst to form the bis (N,N-dialkylamino)alkyl ether, and recovering the bis (N,N-dialkylamino)alkyl ether.

2. The process of claim 1 wherein bis (N,N-dialkylamino)alkyl ether is bis (N,N-dimethylamino)ethyl ether and N,N-dialkylaminoalkanol is N,N-dimethylaminoethanol.

3. The process of claim 1 wherein the heterogeneous solid basic catalyst is a zeolite in an alkali metal cation form.

4. The process of claim 1 wherein the heterogeneous solid basic catalyst is a faujasite type zeolite in an alkali metal cation form.

5. The process of claim 1 wherein the heterogeneous solid basic catalyst is a faujasite type zeolite in an alkali metal cation form wherein the alkali metal is lithium, sodium, potassium, rubidium, or cesium, or mixtures thereof.

6. The process of claim 1 wherein the heterogeneous solid basic catalyst is an X zeolite in an alkali metal cation form.

7. The process of claim 1 wherein the temperature is 250 to 500° C.

8. The process of claim 1 wherein the temperature is 350 to 425° C.

9. A process for producing bis (N,N-dimethylamino)ethyl ether comprising reacting vaporized N,N-dimethylaminoethanol at elevated temperature over a heterogeneous solid basic catalyst to form the bis (N,N-dimethylamino)ethyl ether, and recovering the bis (N,N-dimethylamino)ethyl ether.

10. The process of claim 9 wherein the heterogeneous solid basic catalyst is a faujasite type zeolite in an alkali metal cation form wherein the alkali metal is lithium, sodium, potassium, rubidium, or cesium, or mixtures thereof.

11. The process of claim 9 wherein the heterogeneous solid basic catalyst is an X zeolite in an alkali metal cation form wherein the alkali metal is lithium, sodium, potassium, rubidium, or cesium, or mixtures thereof.

12. The process of claim 9 wherein the temperature is 350 to 425° C.

* * * * *